United States Patent
Yamato et al.

(10) Patent No.: US 6,280,993 B1
(45) Date of Patent: Aug. 28, 2001

(54) GENE ENCODING CLASS I COLLAGENASE

(75) Inventors: Ichiro Yamato, 3-25-33, Yoga, Setagaya-ku, Tokyo 158-0097; Toshiaki Hosaka, Chiba, both of (JP)

(73) Assignee: Ichiro Yamato, Tokyo (JP)

( * ) Notice: Subject to any disclaimer, the term of this patent is extended or adjusted under 35 U.S.C. 154(b) by 0 days.

(21) Appl. No.: 09/379,523

(22) Filed: Aug. 24, 1999

(51) Int. Cl.$^7$ .............................. C12N 9/52; C12N 15/57; C12N 15/70

(52) U.S. Cl. .................. 435/220; 435/69.1; 435/69.7; 435/252.3; 435/252.33; 435/320.1; 536/23.2; 536/23.4

(58) Field of Search ..................................... 435/219, 69.1, 435/220, 69.7, 252.3, 252.33, 320.1; 536/23.2, 23.4

(56) References Cited

FOREIGN PATENT DOCUMENTS

WO 94/00580 * 1/1994 (WO).
WO 98/22574 * 5/1998 (WO).

OTHER PUBLICATIONS

Yoshihara et al., 1994, "Cloning and nucleotide sequence analysis of the colH gene from Clostridium histolyticum encoding a collagenase and a gelatinase", Journal of Bacteriology, vol. 176, pp. 6489–6496.*

Translation of Abstract of Hosaka et al., 1998, "Sequencing of a collagenase gene derived from Clostridium histolyticum, purification of the collagenase, and enzymatic properties thereof", Seikagaku (Biochemistry), vol. 70, p. 1059, Abstract 4P–259.*

Hosaka et al., 1999, GenBank/EMBL/DDJB nucleotide sequence database Accession No. AB 026889, Clostridium histolyticum genomic DNA segment, 3967 nucleotides, submitted title "Class2 collagenase".*

Hosaka et al., 1999, GenBank/EMBL/DDJB translated amino acid sequence, SPTREMBL Accession No. Q9SOXO, Clostridium histolyticum protease, 1118 amino acids, submitted title "Class2 collagenase".*

O. Matsuhita, et al., Journal of Bacteriology, Feb. 1999, vol. 181, pp. 923–933.

* cited by examiner

Primary Examiner—Ponnathapu Achutamurthy
Assistant Examiner—William W. Moore
(74) Attorney, Agent, or Firm—Darby & Darby

(57) ABSTRACT

An isolated DNA encoding a class I collagenase, particularly, the isolated DNA encoding the class I collagenase from *Clostridium histolyticum*, a vector containing the gene, a transformant containing the vector, a class I collagenase, and a method of preparing the class I collagenase are disclosed.

15 Claims, 1 Drawing Sheet

GENE ENCODING CLASS I COLLAGENASE

BACKGROUND OF THE INVENTION

1. Field of the Invention

The present invention relates to a gene encoding a class I collagenase, a vector containing the gene, a transformant containing the vector, a class I collagenase, and a method of preparing the class I collagenase.

2. Description of the Related Art

Collagenases belong to a hydrolase, and act on a collagen to decompose a peptide bond. These collagenases play an important role in biotechnology, for example, in a culture of an excised tissue or a cell. In particular, collagenases from Clostridium species are important because they exhibit a reactivity useful in protein engineering. It is known that collagenases from *Clostridium histolyticum* include the class I and class II collagenases, and that the class I collagenase has a high specificity to a naturally occurring collagen and the class II collagenase has a high specificity to a synthesized peptide. Further, a gene encoding the class II collagenase has been cloned.

Nevertheless, the structure of the class I collagenase from *Clostridium histolyticum* is not known, and the gene encoding the class I collagenase from *Clostridium histolyticum* has not been isolated.

SUMMARY OF THE INVENTION

The present invention is based upon an isolation of the gene encoding the class I collagenase from *Clostridium histolyticum*. Accordingly, the object of the present invention is to provide an isolated DNA encoding the class I collagenase. Other objects and advantages will be apparent from the following description.

In accordance with the present invention, there is provided an isolated DNA encoding a class I collagenase, particularly, an isolated DNA encoding a class I collagenase from *Clostridium histolyticum*.

Further, in accordance with the present invention, there is provided a vector comprising the isolated DNA encoding the class I collagenase, particularly, the isolated DNA encoding the class I collagenase from *Clostridium histolyticum*.

Still further, in accordance with the present invention, there is provided a transformant comprising the vector.

Still further, in accordance with the present invention, there is provided a class I collagenase or a functional equivalent thereof.

Still further, in accordance with the present invention, there is provided a method of preparing a class I collagenase or a functional equivalent thereof by culturing the transformant.

Figure 1:
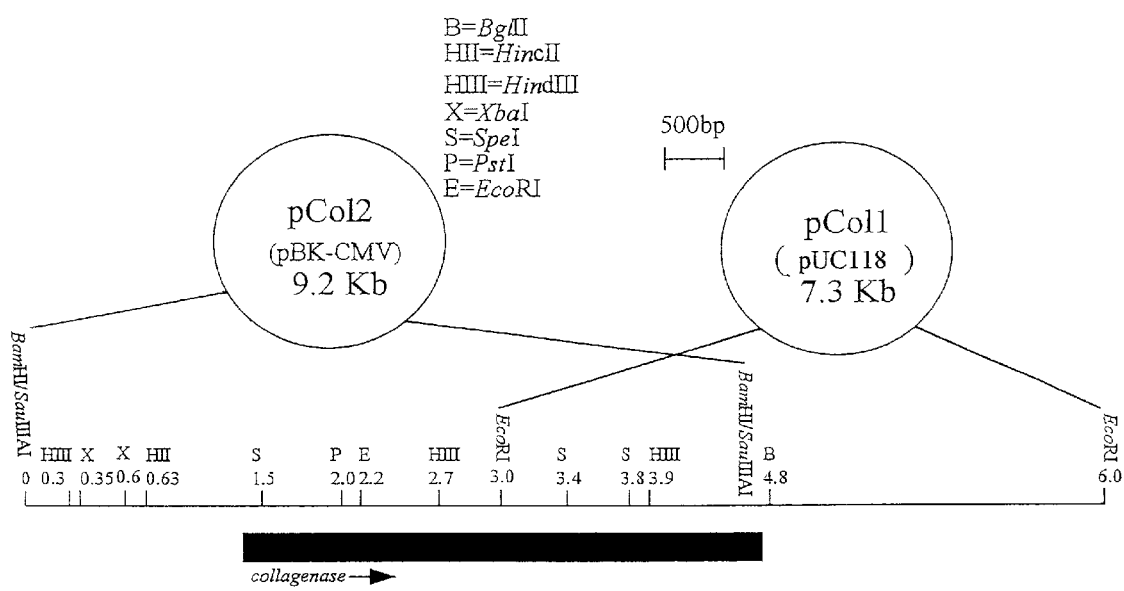
FIG. 1 is a restriction map of pCol1 and pCol2.

DESCRIPTION OF THE PREFERRED EMBODIMENTS (A) Isolation of the Gene Encoding the Class I Collagenase (1) A Genomic DNA Library of *Clostridium histolyticum*

As a donor of the gene encoding the class I collagenase, *Clostridium histolyticum* (JCM1403) can be used. The *Clostridium histolyticum* strain can be cultured in a conventional method of culturing anaerobically to a stationary phase in a GAM medium.

A genomic DNA can be prepared by an alkali method described in "Molecular Cloning", pages 89–91, Cold Spring Harbor Laboratory (1982). For example, a genomic DNA having a high molecular weight is partially digested with EcoRI or Sau3AI. The digested DNA fragments are subjected to a sucrose density gradient centrifugation as described in "Molecular Cloning" (supra). Fractions containing DNA fragments having approximately 5 kb are collected. Using a T4 ligase, DNA fragments digested with EcoRI are ligated to an EcoRI site in λgt11, and DNA fragments digested with Sau3AI are ligated to a BamHI site in a λ ZAP EXPRESS vector. The ligation product is packaged using a Gigapack III Packaging Kit to prepare λgt11 or λ ZAP EXPRESS phage libraries of the genomic DNA.

(2) Isolation of the Class I Collagenase Gene In Parts

An antibody to collagenase is used to isolate a clone expressing a part of collagenase from the expression λgt11 phage library containing chromosome fragments from *Clostridium histolyticum*. The antibody is prepared by sensitizing an SPF rabbit with a commercially available collagenase from *Clostridium histolyticum*. The antibody may be prepared by the method described in Hanada, et al., J. Biol. Chem. 263, 7181–7185 (1988).

A DNA fragment obtained from the clone isolated by detection with the antibody is labeled. The labeled DNA fragment is then used to isolate another clone expressing another part of collagenase from the λ ZAP EXPRESS phage library containing chromosome fragments from *Clostridium histolyticum*, by a plaque hybridization. The labeling of the DNA fragment and the detection of the hybridization can be carried out as described in "Molecular Cloning", pages 320–328, Cold Spring Harbor Laboratory (1982).

(3) Sequencing

The isolated λgt11 clone is digested with EcoRI to obtain digested fragments, and the digested fragments are subcloned in an EcoRI site of pUC118, pUC119 or the like. On the other hand, plasmids are prepared from the isolated λ ZAP EXPRESS phage clone by the method described in a manual of the ZAP EXPRESS cloning kit. Several plasmids are then digested with restriction enzymes to prepare a restriction enzyme map. On the basis of the restriction enzyme map, subclone plasmids having a part of an inserted fragment are prepared. An autocycle Sequencing kit and ALF DNA sequencer are used to determine base sequences of the subclone plasmids, and the resulting base sequences are analyzed to determine a base sequence of SEQ ID NO: 2. Further, an amino acid sequence of a polypeptide encoded by the gene is deduced as SEQ ID NO: 1 from the base sequence of SEQ ID NO: 2.

(B) The Class I Collagenase and the Gene Encoding the Same

As used herein, the term class I collagenase from *Clostridium histolyticum* means a polypeptide having 1118 amino acids of SEQ ID NO: 1. It is considered that the class I collagenase of SEQ ID NO: 1 is a premature protein, and contains a signal peptide consisting of the first to 109th amino acids of SEQ ID NO: 1, whereas a matured class I collagenase from *Clostridium histolyticum* consists of the 110th to 1118th amino acids of SEQ ID NO: 1.

As used herein, the term "functional equivalent" of the class I collagenase refers to a polypeptide having an activity substantially the same as the activity of the class I collagenase. To prepare the functional equivalent of the class I collagenase, one or more amino acids can be deleted from, replaced with, and/or added to the amino acid sequence of SEQ ID NO: 1 by conventional methods.

A fused gene containing the class I collagenase gene and a known peptide gene, such as a glutatione-S-transferase (GST) gene, can be easily prepared by conventional methods. Such a fused gene can be inserted by conventional DNA recombination techniques into an expression vector, which can be controlled by an expression in *E. coli,* such as pUC118 or pUC119 containing a promoter-operator site of a lactose operon. There is a high probability that the fused DNA will encode a polypeptide exhibiting a collagenase activity. The fused DNA encoding a polypeptide exhibiting a collagenase activity can be selected from a transformant.

A gene substantially equivalent to the class I collagenase gene can be obtained by carrying out a hybridization under a stringent condition with a probe containing at least a part of the DNA sequence of SEQ No. 2 or a complementary DNA sequence thereof, and selecting a gene encoding a polypeptide having a collagenase activity. The stringent condition means a condition whereby only a specific hybridization is selectively formed, and a signal can be detected, but a non-specific hybridization is not formed. Although the stringent condition varies with a species, it can be easily determined by examining salt concentrations and temperatures during the hybridization and washing in accordance with conventional methods. For example, specific signals can be detected under the condition as shown in Example 1(9). Therefore, the hybridization can be carried out, using 6×SSPE, 5×Denhardt's reagent, 0.4% (w/v) SDS, and denatured salmon sperm DNA (500 μg/ml), overnight (8 to 16 hours), and the washing carried out with 2×SSPE and 0.1% (w/v) SDS for 2.5 hours. The temperature during the hybridization and washing may be 45° C. or more, preferably 52° C. or more, more preferably 57° C. or more. There is a high probability that the DNA hybridized under such a stringent condition will encode a polypeptide showing a collagenase activity. The collagenase activity of the polypeptide encoded by the hybridized DNA can be easily examined by preparing a transformant.

The class I collagenase can be expressed by transforming *E. coli* with the isolated gene, culturing the transformant in a nutrient medium, inducing an expression, harvesting and suspending *E. coli,* disrupting *E. coli* with, for example, an ultrasonic treatment, and purifying the class I collagenase from a supernatant. When the class I collagenase is expressed as a fused protein, properties of a fusing partner can be used to simply and efficiently purify the fused protein. For example, a fused protein with a glutatione-S-transferase (GST) can be purified in one step, using a glutathione sepharose affinity column.

(C) Collagenase Activity

The collagenase activity of the class I collagenase may be measured in accordance with, for example, a known method described in Wunsch and Heidrich, Z. Physiol. Chem., 333, 149–151 (1963) as follows:

In this method, PZ-peptide (4-phenylazobenzyloxy carbonylprolyl-leucyl-glycyl-prolyl-D-arginine) is used as a substrate, and the following solutions are prepared before measurement:

Solution A: 1.287 mM of a PZ-peptide solution in a 50 mM Tris-HCl (pH 7.5) (final concentration of the substrate in a reaction mixture=1.03 mM),
Solution B: an aqueous solution of a 10 mM calcium acetate,
Solution C: a 0.5% (w/v) potassium citrate buffer (pH 3.5), and
Solution D: ethyl acetate.

Two centrifugation tubes are used for an enzyme sample: one is a tube for reference and the other is a tube for measurement. To each of the two tubes, 490 μl of the Solution B is added, and then 10 μl of a sample containing the class I collagenase is added. Only one tube for reference is incubated at 70° C. for 15 minutes, to inactivate the enzyme. To each of the two tubes, 2.0 ml of the Solution A at 37° C. is added, and then each of the mixtures is stirred and incubated at 37° C. After 5 to 30 minutes of an enzyme reaction, 0.5 ml of each of the mixtures is taken and poured into new tubes each containing 1 ml of the Solution C and the whole stirred to stop the enzyme reaction. Further, 5 ml of the Solution D is added and stirred. Therefore, 4 ml of each of the ethyl acetate layers is taken and poured into each of the two tubes, and 0.3 g of $Na_2SO_4$ is added. An optical density at 320 nm of each of the supernatants is measured. If 1 unit of the collagenase activity is defined as an activity releasing 1 μmol of 4-phenylazobenzyloxycarbonyl-prolyl-leucine for 1 minute, the collagenase activity can be calculated by the following equation:

$$A(\text{units}) = (OD_M - OD_R) \times (0.23/T)$$

wherein A is the collagenase activity, $OD_M$ is an optical density at 320 nm of the sample in the tube for measurement, $OD_R$ is an optical density at 320 nm of the sample in the tube for reference, and T is a reaction time.

EXAMPLES

The present invention now will be further illustrated by, but is by no means limited to, the following Examples.

Example 1

Cloning of a Class I Collagenase Gene (1) Preparation of a Rabbit Antibody to Collagenases A collagenase fraction (30 μg, 0.1 ml) containing the class I and class II collagenases from *Clostridium histolyticum* (Collagenase Type III; Sigma Chemicals) derived from *Clostridium histolyticum* was mixed with an equal volume of a complete Freund adjuvant, and the resulting mixture was injected subcutaneously to an SPF (specific pathogen free) rabbit. After 10 days from the first injection, a mixture of collagenase (3 μg, 0.1 ml) and an incomplete Freund adjuvant (0.1 ml) was injected subcutaneously to the rabbit. Then, the same procedure was repeated, as a booster, at intervals of approximately 10 days. After 40 days from the first injection, a first blood sample was taken from an ear of the rabbit and an antibody titer of a serum of the sample was determined by reacting the collagenase (1 μg/10 μl) with a dilution series of the serum (10 μl) diluted with a physiological saline, and detecting a formation of diffusion precipitation lines on an agarose gel [Ouchterlony double diffusion test; "Jikken Seibutsugaku Koza (Lecture on Experimental Biology), Vol. 14, Immunobiology", pages 78–82]. Further, the antigen (collagenase) was subjected to sodium dodecyl sulfate polyacrylamide gel electrophoresis (SDS-PAGE), and then a western blotting was carried out to determine a reactivity of the antibody in the serum.

(2) Preparation of a Genomic DNA Library of *Clostridium histolyticum*

*Clostridium histolyticum* (JCM1403) was cultured to a stationary phase in 100 ml of GAM medium (Nissui Seiyaku) at 37° C. for about 24 hours, and then a genomic DNA (30 μg) was prepared by the alkali method described in "Molecular Cloning", pages 89–91, Cold Spring Harbor Laboratory (1982). A part (10 μg) of the resulting genomic DNA was partially digested with EcoRI (500 units; Takara Shuzo) in 500 μl of an EcoRI* buffer [25 mM Tris-HCl (pH 8.5), 2 mM $MgCl_2$, and 20% glycerol] at 37° C. for 15 minutes so that an average length of the resulting DNA fragments was approximately 5 kb. The digested DNA fragments were subjected to a sucrose density gradient centrifugation to collect a fraction containing DNA fragments having a length of approximately 5 kb. The DNA fragments in the fraction (200 ng) were ligated to a λgt11 (2 μg) which had been digested with EcoRI using a T4 DNA ligase (Takara Shuzo). The ligation product was packaged using a Gigapack III Packaging Kit (STRATAGENE), and amplified using an *Escherichia coli* K-12 strain Y1089 as a host to prepare a λgt11 phage library of the genomic DNA.

Another part (10 μg) of the above genomic DNA prepared from *Clostridium histolyticum* (JCM1403) was partially digested with Sau3AI (8 units; Takara Shuzo) in 500 μl of an H buffer [50 mM Tris-HCl (pH 7.5), 10 mM $MgCl_2$, 1 mM dithiothreitol (DTT), and 100 mM NaCl] at 16° C. for 180 minutes so that an average length of the resulting DNA fragments was approximately 10 kb. The digested DNA fragments were subjected to a sucrose density gradient centrifugation to collect a fraction containing DNA fragments having a length of approximately 4–8 kb. The DNA fragments in the fraction were ligated to a λ ZAP Express vector and the ligation product was packaged using a ZAP Express Predigested Gigapack III Cloning Kit (STRATAGENE), and amplified using an *E. coli* XL1-Blue as a host to prepare a λ ZAP EXPRESS phage library of the genomic DNA.

(3) Detection of λgt11 Phage Clones Using the Antibody

The λgt11 phage library prepared in Example 1(2) was used to form plaques on an agar plate. A nitrocellulose filter was mounted on the agar plate for several minutes, and then carefully removed from the agar plate. The nitrocellulose filter was dipped in 10 ml of a TBST solution [50 mM Tris-HCl (pH 8.0), 150 mM NaCl, and 0.05% Tween20] containing 10% skim milk at 4° C. overnight. The anti-collagenase antibody (10 μl) prepared in Example 1(1) was added to the solution. After the addition of the antibody, the nitrocellulose filter was shaken at room temperature for 1 hour, and washed four times with 10 ml of the TBST solution for 5 minutes. The nitrocellulose filter was further shaken in 10 ml of a buffer [10 mM Tris-HCl (pH 8.0) and 125 mM NaCl] containing 5 μl of a goat anti-rabbit IgG (Jackson Immuno Research LABORATORIES) labeled with alkaline phosphatase as a second antibody at room temperature for 1 hour, and washed four times with 10 ml of the TBST solution for 5 minutes and once with hyperpure water. The nitrocellulose filter was dipped in 10 ml of a staining solution [100 mM Tris-HCl (pH 9.5), 100 mM NaCl, 5 mM $MgCl_2$, 66 μl of 61.15 mM nitro blue tetrazolium (Wako Pure Chemical Industries), and 33 μl of 115.3 mM 5-bromo-4-chloro-3-indolylphosphate p-toluidine salt (Wako Pure Chemical Industries)] for 5–60 minutes. After coloring, 10 ml of a stopping solution [20 mM Tris-HCl (pH 8.0) and 5 mM EDTA] was added to stop the reaction, and the nitrocellulose filter was dried. As a result, a positive clone was detected.

(4) Recovery of a Phage DNA from a Positive Plaque Detected by the Antibody

An overnight culture liquid (50 μl) of an *E. coli* K-12 strain Y1089 was added to a λ broth medium (5 ml), and further cultured with shaking at 37° C. for about 2 hours. A soft agar portion (diameter=approximately 5 mm) containing the positive plaque detected in Example 1(3) was cut out from the agar plate and added to the culture liquid (5 ml). The whole was cultured with shaking at 37° C., while the turbidity of the culture liquid was periodically measured. When a stationary phase was observed, the culture liquid was diluted with a 20-fold volume of the medium, and the culturing was continued. When a lysis of the *E. coli* occurred and the turbidity was lowered, chloroform (50 μl) was added to the culture liquid, and the whole was allowed to stand at 37° C. for 30 minutes. The culture liquid was centrifuged at 1000×g for 15 minutes (room temperature) to obtain a phage solution as a supernatant.

(5) Large-scale Preparation of a Phage DNA

An overnight culture liquid (5 ml) of *E. coli* K-12 strain Y1089 was added to a λ broth medium (500 ml), and further cultured while shaken at 37° C. for about 2 hours. The phage solution prepared in Example 1(4) was added to the culture liquid so that a ratio of the phage to the *E. coli* was 1:1 and the whole was cultured while shaken. When a lysis of *E. coli* occurred as described in Example 1(4), chloroform (1 ml) was added to the culture liquid, the whole was allowed to stand for 30 minutes, and then centrifuged at 1000×g for 15 minutes to obtain a supernatant. To the resulting supernatant, 1 μg/ml of DNaseI (Takara Shuzo) and 1 μg/ml of RNaseI (Nippon gene) were added, and the mixture was incubated at 37° C. for 1 hour. Further, NaCl and polyethylene glycol (PEG) 4000 were gradually added and dissolved so that the concentration of NaCl became 1 M and that of the PEG4000 became 20%. The mixture was allowed to stand at 4° C. for 1 hour, and then centrifuged at 10000×g for 40 minutes (4° C.) to obtain a precipitate. The precipitate was dissolved in 10 ml of a TM buffer [50 mM Tris-HCl (pH 7.5) and 10 mM $MgCl_2$]. The solution was centrifuged at 10000×g for 30 minutes (4° C.) to obtain a supernatant, and then the resulting supernatant was further centrifuged at 80000×g for 1 hour (4° C.) to obtain phage particles. The phage particles were dissolved in 2 ml of the TM buffer. To the solution, 2 ml of phenol saturated with water was added, and the mixture was gently stirred at room temperature for 30 minutes. After centrifugation of the mixture at 1000×g for 15 minutes, a phenol phase was removed, and 2 ml of phenol saturated with water was added. The mixture then was stirred gently and centrifuged to collect an aqueous phase. An equal volume of chloroform/phenol (1:1) was then added to the aqueous phase, and after stirring, the resulting aqueous phase was collected. NaCl was then added to the aqueous phase, so that the concentration of NaCl became 0.1 M, and then cold ethanol added so that the final concentration of ethanol became 70% to precipitate DNA. The whole was then centrifuged at 10000×g for 10 minutes (4° C.) to obtain a precipitate, and the precipitate was dissolved in 0.5 ml of a TE buffer [10 mM Tris-HCl (pH 7.5) and 1 mM EDTA] to prepare a phage DNA solution.

(6) Isolation of a Part of a Class I Collagenase Gene

The phage DNA solution (1 μg) prepared in Example 1(5) and containing the isolated phage DNA, and pUC118 (400 ng) were digested with 5 units of EcoRI (Takara Shuzo) in the H buffer at 37° C. for 2 hours. The reaction mixtures were then subjected to a 0.7% agarose gel electrophoresis to separate digested products. From the reaction mixture containing the phage DNA, an approximately 3 kb DNA fragment was obtained, and from one containing pUC118, an approximately 4 kb DNA fragment was obtained, respectively. A GENECLEAN II KIT (BIO 101) was used to obtain the DNA fragments from the agarose gel. More particularly, a part of the agarose gel (2.0 cm×0.5 cm×0.5 cm) was taken and then charged to a microcentrifugation tube. After the weight of the part was measured, a three-fold weight of an NaI solution was added and the whole was incubated at 50° C. for 10 minutes. Further, 5 μl of Glass milk attached to the kit was added, and the mixture was stirred and cooled on ice. After 5 minutes, the mixture was centrifuged at 10000×g for 5 seconds and a supernatant was discarded. The Glass milk was washed four times with 200 μl of New wash attached to the kit. Further, the Glass milk was suspended in 50 μl of the TE buffer and the suspension was incubated at 50° C. for 10 minutes. The suspension was then centrifuged to obtain a supernatant as a DNA solution.

Using a TAKARA Ligation Kit (Takara Shuzo), the 3 kb EcoRI fragment (50 ng) derived from the phage DNA and the 4 kb EcoRI fragment (30 ng) of pUC118 were ligated. An overnight culture liquid of an *E. coli* JM109 strain was diluted to 100-fold volume with 20 ml of an LB medium and cultured with shaking at 37° C. After 2 hours, the *E. coli* was collected and suspended in the LB medium containing 50 mM $MgCl_2$, 10% PEG6000, and 5% dimethylsulfoxide (DMSO). The suspension (200 μl) was then mixed with the ligated plasmid DNA, and cooled on ice for 40 minutes. Further, the mixture was incubated at 42° C. for 90 seconds and cooled on ice for 10 minutes. Thereafter, the LB medium (600 μl) was added and the whole was cultured at 37° C. for 40 minutes. Transformants containing the ligated plasmid DNA were selected on an L agar medium containing 50 μg/ml of ampicillin. The resulting plasmid was named pCol1.

(7) Large-scale Preparation and Sequencing of pCol1

A plasmid pCol1 was prepared from an overnight culture liquid (250 ml, LB medium) of the transformant containing pCol1, in accordance with the method described in "Molecular Cloning", pages 86–94, Cold Spring Harbor Laboratory (1982). Specifically, the transformant was collected by centrifugation at 10000×g for 10 minutes (4° C.), suspended in 5 ml of an A solution [25 mM Tris-HCl (pH 7.5), 10% glucose, and 10 mM EDTA] containing lysozyme (5 mg), and cooled on ice for 10 minutes. Further, 10 ml of a B solution (1% SDS and 0.2 N NaOH) was added to the mixture and the whole cooled on ice for 10 minutes. Furthermore, 7.5 ml of a C solution (3 M potassium acetate and 6.7 M acetic acid) was added and the whole cooled on ice for 10 minutes. After centrifugation at 35000×g for 30 minutes (4° C.), a supernatant was taken to another centrifugation tube, and 13.5 ml of 2-propanol (Wako Pure Chemical Industries) was added to the tube. After incubation at room temperature for 15 minutes and centrifugation at 25000×g for 30 minutes (room temperature), a supernatant was removed, and a precipitate was washed with 70% of cold ethanol and dried by vacuum drying. The TE buffer (4.2 ml), cesium chloride (4.4 g), and 10 mg/μl ethidium bromide (200 μl) were added to the precipitate, and the mixture was taken to an OptiSeal centrifugation tube (BECKMAN) and centrifuged at 400000×g for 300 minutes (20° C.) to collect a band of plasmid separated by a cesium chloride density-gradient centrifugation. Ethidium bromide was removed from the plasmid, using saturated 1-butanol, and the plasmid was dialyzed twice with 1 liter of the TE buffer.

Deletion of the resulting plasmid pCol1 was carried out using a Kilo-sequence Deletion Kit (Takara Shuzo). A series of deleted plasmids was prepared in accordance with a manual attached to the kit. Specifically, pCol1 (500 ng) was digested with BamHI in a B buffer [10 mM Tris-HCl (pH 8.5), 5 mM $MgCl_2$, 1 mM mercaptoethanol, and 100 mM NaCl; Nippon gene] and with PstI in the H buffer (Nippon gene). Further, at appropriate intervals after Mung Bean Nuclease (Nippon gene) was added to the digested pCol1, a part of the reaction mixture was periodically taken out and the reaction of Mung Bean Nuclease was stopped, successively, to prepare the deletion series. The resulting deletion series was blunted with a Klenow fragment of *E. coli* DNA polymerase I and ligated with a T4 DNA ligase. The *E. coli* was then transformed with each of the ligated deletion series, and plasmid DNAs of the deletion series were prepared from the resulting transformants. The base sequence of each of the plasmid DNAs was determined by a dideoxy method in accordance with a manual attached to a Sequencing Kit (Takara Shuzo). As a label, [$\alpha$-$^{32}$P] dCTP (111 TBq/ml; Amersham Japan) was used.

As a result, the DNA fragment in pCol1, i.e., the DNA fragment derived from the positive clone detected in Example 1(3), had a novel base sequence. Namely, the base sequence did not have a homology to known base sequences, including that of a class II collagenase gene. Further, the isolated novel DNA fragment contained a 1683 bp of a base sequence which appears to be a portion of the 3' region of a structural gene, and a base sequence which appears to form a palindrome structure, downstream of the stop codon of the structural gene.

(8) Preparation of a Probe

A plasmid pCol1 (5 μg) prepared in Example 1(7) was digested with EcoRI in the H buffer and with HindIII in the B buffer (Nippon gene) at 37° C. for 3 hours, and subjected to a 0.7% agarose gel electrophoresis. The above-mentioned GENECLEAN II KIT was used to prepare a 900 bp EcoRI-HindIII fragment from the DNA fragment containing the novel base sequence in pCol1. The EcoRI-HindIII fragment (200 ng) was labeled with [$\gamma$-$^{32}$P] ATP (111 TBq/ml; Amersham Japan) using a random primer labeling kit (Takara Shuzo) in accordance with a manual attached to the kit. This probe was used in the following plaque hybridization.

(9) Screening of the λ ZAP EXPRESS Phage Library

An overnight culture liquid (0.1 ml) of *E. coli* XL1-Blue was infected with 1 μl of a λ ZAP EXPRESS phage library of the genomic DNA prepared in Example 1(2) and incubated on a soft agar plate at 37° C. overnight. As described in Example 1(3), DNAs on the soft agar plate were transferred to a nylon transfer membrane (HyBond-N+; Amersham).

A hybridization was carried out on the membrane using the isotope-labeled probe prepared in Example 1(8) in accordance with a manual attached to ZAP Express. Specifically, the membrane carrying DNAs attached thereto was dipped in a standard prehybridization buffer [6×SSPE (1.08 M sodium chloride, 0.06 M sodium phosphate, and 6 mM EDTA; pH 7.4), 5×Denhardt's reagent (0.1% polyvinylpyrrolidone, 0.1% Ficoll, and 0.1% bovine serum albumin), 0.4% (w/v) SDS, and 500 μg/ml denatured salmon sperm DNA], and thereafter, the membrane was allowed to stand at 37° C. for 1 hour while being gently shaken. Further, the probe, which had been boiled at 100° C. for 10 minutes and rapidly cooled with ice water, was added to the buffer and the membrane was further allowed to stand at 37° C. for 12 hours while gently shaken. After the hybridization was completed, the membrane was taken to a new vessel and washed with a washing solution [2×SSPE and 0.1% (w/v) SDS] at 52° C. for 2.5 hours. The membrane was exposed to an imaging plate (FUJI IMAGING PLATE TYPE BAS-III; Fuji Photo Film), and five positive signals were detected on the membrane and named positive clones A to E. Soft agar portions (diameter=5 mm) corresponding to these positive signals were cut out from the agar plate, and charged to microcentrifugation tubes. To the tubes, 500 μl of an SM buffer [50 mM Tris-HCl (pH 7.5), 10 mM NaCl, 0.2% (w/v) $MgSO_4.7H_2O$, and 0.01% gelatin] and 20 μl of chloroform were added and the whole allowed to stand at 4° C. overnight. Plaques were formed on agar plates, under the condition that approximately 100 plaques were formed on a plate. These plaques were transferred to nylon membranes and a hybridization was carried out using the probe, as described above. For the phage solution derived from the positive clone A, many strong signals were detected. For one derived from the positive clone B, no signal was detected, and for those derived from the positive clones C, D, and E, several signals were detected.

Therefore, plaques having the positive signals from the clones A, C, D, and E were recovered and a plaque hybridization was carried out again. As a result, all plaques derived from the clones A and D were positive.

Using the phage clones A and D, an in vivo excision was carried out in accordance with a manual attached to the λ ZAP EXPRESS Cloning kit, to subclone the DNA fragment in the phage clones into PBK-CMV (STRATAGENE). Specifically, E. coli XL1-Blue was infected with the phage clones A and D and a helper phage attached to the kit, and sowed on an L agar plate containing 50 μg/ml of kanamycin. In the E. coli, a DNA fragment excised from a phage can be maintained in the form of a plasmid, and a large-scale preparation of the plasmids revealed that the DNA fragment from the phage clone A was the same as that from the phage clone D. The plasmid containing the DNA fragment was named pCol2.

Example 2
Analysis of a Class I Collagenase Gene
(1) Preparation of a Restriction Map In accordance with the method described in Example 1(7), plasmid pCol2 was prepared in a large scale. The plasmid pCol1 (200 ng) prepared in Example 1(7) and plasmid pCol2 (200 ng) were digested with one (5 units) of the following restriction enzymes in an appropriate buffer (20 μl) at 37° C. for 1 hour. The combinations of the restriction enzymes and the buffers were as follows: EcoRI and an H buffer, HindIII and a B buffer, PstI and an H buffer, SpeI and an M buffer [10 mM Tris-HCl (pH 7.5), 10 mM MgCl$_2$, 1 mM DTT, and 50 mM NaCl; Nippon gene], and XbaI and an M buffer. After digestion, the mixtures were subjected to a 0.7% agarose gel electrophoresis, and the size of the digested fragments was determined. A restriction map of pCol1 and pCol2 is shown in FIG. 1.
(2) Sequencing of pCol2

Digested fragments from pCol2 were subcloned into plasmid pBluescriptII KS+ (TOYOBO). These fragments were prepared on the basis of the restriction map of pCol2, and the subcloning was carried out as mentioned above. After transformation, plasmids containing digested fragments were prepared from transformants. The sequencing of these plasmids was carried out using an AutoCycle Sequencing Kit (Pharmacia) and A. L. F. DNA Sequencer II (Pharmacia) in accordance with a manual attached to the kit. For some subcloned fragments whose base sequences could not be completely determined, some primers (Nippon Bioservice) were synthesized on the basis of base sequences partially determined whereby the remaining base sequences were completely determined. The primers were labeled with fluorescein isothiocyanate (FITC). As a result, it was found that pCol2 contained a portion of a novel structural gene without 81 bp of a 3' terminus thereof.
(3) Preparation of a Full-length Class I Collagenase Gene Plasmid pCol2 was digested with HincII in the M buffer and with BamHI in the B buffer. The HincII-BamHI fragment was subcloned into plasmid pBluescriptII KS+, and the resulting plasmid was named pBCol2. The plasmid pBCol2 was digested with BamHI in the B buffer, and partially digested with EcoRI in the H buffer. Then 5.4 kb BamHI-EcoRI fragment which contains pBluescriptII KS+ vector portion and lacks 1.7 kb 3' portion of collagenase gene was separated from five digested fragments (0.8 kb, 1.7 kb, 2.5 kb, 4.6 kb, and 5.4 kb).

The plasmid pCol1 was digested with EcoRI and BglII in the H buffer, and the 1.7 kb EcoRI-BglII fragment was separated from three digested fragments (1.7 kb, 1.3 kb, and 4.1 kb). The 1.7 kb EcoRI-BglII fragment was ligated to the 5.4 kb BamHI-EcoRI fragment derived from plasmid pCol2 with T4 ligase (Nippon gene). The resulting plasmid containing a full length of the novel structural gene was named pCol. The base sequence of the novel structural gene is the sequence of SEQ ID NO: 2. Further, an amino acid sequence of a polypeptide encoded by the gene is deduced as SEQ ID NO: 1 from the base sequence of SEQ ID NO: 2.

Example 3
Preparation of a Vector for Expression of a Fusion Protein with Glutatione-S-transferase (GST)
(1) Amplification of a part of the class I collagenase gene On the basis of the base sequence of the class I collagenase gene, two primers for introducing recognition sites of restriction enzymes were synthesized (Nippon Bioservice) as follows: Primer 5' BamHI&PstI-P having the base sequence:

CTAAATCAA<u>CTGCAG</u>GAAGT<u>GGATCC</u>ATAGCGAATAC, and Primer 3' PstI-P having the base sequence:

CTTGAA<u>CTGCAG</u>TTCCTAGC. One underlined sequence "CTGCAG" is a PstI recognition site and the other underlined sequence "GGATCC" is a BamHI recognition site. These primers were designed so that a partial fragment of the class I collagenase from the 1st amino acid to the 109th amino acid was replaced with a different gene, and the remaining partial fragment of the class I collagenase gene starting from the 110th amino acid of the amino acid sequence of SEQ ID NO: 1 was fused to the replaced gene. This is because the 5' end partial fragment from the 1st to 109th amino acids appeared to be a signal region. Using the Primers 5' BamHI&PstI-P and 3' PstI-P and plasmid pCol (300 ng) as a template, a polymerase chain reaction (PCR) was performed to amplify a part of the class I collagenase gene. Specifically, 76.5 μl of sterilized distilled water, 10 μl of a 10×buffer [attached to Gene Taq (Nippon gene)], 1 μl of a 100 pmol/μl Primer 5' BamHI&PstI-P, 1 μl of a 100 pmol/μl Primer 3' PstI-P, 3 μl of a 100 μg/ml plasmid pCol, 8 μl of a 2.5 mM DNTP solution (attached to Gene Taq), and 0.5 μl of a Gene Taq (Nippon gene) were mixed in a 0.2 ml volume of a PCR tube (Nippon Genetics) and the tube set in a Programmable Thermal Controller (MJ RESEARCH). The PCR was carried out by heating at 92° C. for 7 minutes and repeating a cycle of denaturation at 95° C. for 1 minute, primer annealing at 72° C. for 2.5 minutes, and synthesis at 55° C. for 2 minutes in 20 cycles. After the reaction was completed, 2 μl of the reaction solution was subjected to a 0.7% agarose gel electrophoresis to find an approximately 400 bp DNA fragment as an amplified product.

The solution containing the amplified product (200 μl) was subjected to a 0.7% agarose gel electrophoresis to collect the 400 bp DNA fragment from the gel using SUPREC-01 (Takara Shuzo). The DNA fragment was eluted with 400 μl of the TE buffer from a spin column, precipitated with ethanol, and dissolved in a TE solution. The DNA fragment solution (50 μl) was then digested with PstI, and subjected to 0.7% agarose gel electrophoresis to collect the 400 bp PstI fragment. The plasmid pCol (200 ng) was digested with PstI, treated with 1 unit of a bacterial alkaline phosphatase (BAP; Nippon gene) in 50 μl of a BAP buffer [50 mM Tris-HCl (pH 9.0) and 1 mM MgCl$_2$] at 55° C. for 1 hour, and subjected to a 0.7% agarose gel electrophoresis to collect the PstI fragment. The 400 bp PstI fragment was ligated to the PstI fragment derived from plasmid pCol with T4 DNA ligase, to integrate the PCR amplified fragment into the plasmid pCol. The resulting plasmid was named pCCol-1. The base sequence was determined with an A. L. F. DNA Sequencer II to select a plasmid containing the fragment inserted in a right direction.

(2) Preparation of a GST-class I Collagenase Fusion Gene

The plasmid pGEX-2TK (a vector for expressing GST; Pharmacia) and the plasmid pCCol-1 prepared in Example 3(1) were digested with BamHI in the B buffer, and SacI in an L buffer [10 mM Tris-HCl (pH 7.5), 10 mM MgCl$_2$, and 1 mM DTT; Nippon gene], and subjected to a 0.7% agarose gel electrophoresis, respectively, and BamHI-SacI fragments were collected. These BamHI-SacI fragments were ligated with a T4 DNA ligase to integrate a part of the class I collagenase gene into the plasmid pGEX-2TK. The resulting plasmid contained a GST-class I collagenase fusion gene whereby GST was fused to the N terminus of the class I collagenase, and named pGCol-1.

Example 4

Expression and Purification of the GST-class I Collagenase Fusion Protein (1) Expression Induction of the GST-class I Collagenase Fusion Protein An *E. coli* JM109 strain was transformed with the plasmid pGCol-1 prepared in Example 3(2), and the resulting transformant was used to express the GST-class I collagenase fusion protein. Specifically, the transformant was inoculated to 10 ml of an LB medium [a 10 g/liter tryptone (DIFCO), a 5 g/liter yeast extract (DIFCO), and a 5 g/liter NaCl] containing ampicillin (final concentration=50 μg/ml; Meiji Seika) and incubated, with shaking at 30° C. overnight. The overnight culture liquid was taken and charged to 1 liter of the LB medium containing ampicillin and the whole was incubated, while shaken vigorously, at 30° C. When the value of OD$_{600}$ became more than 0.4, isopropyl-β-thiogalactoside (IPTG; NOVA biochem) was added so that the final concentration thereof became 0.2 mM, and then the culture liquid was incubated, while shaken vigorously, at 30° C. for 3 hours.

The culture liquid was centrifuged at 10000×g for 10 minutes (4° C.) using a HIMAC CENTRIFUGE Type SCR20B (Hitachi Koki) to collect the *E. coli* transformant. The collected transformant was washed once with 250 ml of 50 mM Tris-HCl (pH 7.5) and 10 mM CaCl$_2$, and suspended in 5 ml of 50 mM Tris-HCl (pH 7.5) and 10 mM CaCl$_2$. 1 μl of 1 μg/μl DNaseI was added to the suspension, and the mixture treated by ultrasonication [Sonifier 250 (BRANSON), at maximum output for 5 minutes, 6 times] on ice. The treated mixture was then centrifuged at 210000×g for 30 minutes [4° C.; Type 70P-72 (Hitachi Koki)] to obtain a crude extract as a supernatant.

(2) Purification with an Affinity Column

The crude extract prepared in Example 4(1) was subjected to a glutathione sepharose column (2 ml; Pharmacia) in accordance with a manual attached to the column. Specifically, the column (size=2 ml) was washed with a solution containing 50 mM Tris-HCl (pH 8.0) and 0.14 M NaCl, and a sample applied. After 10 minutes, the column was washed with the solution containing 50 mM Tris-HCl (pH 8.0) and 0.14 M NaCl. When absorbance at 280 nm reached approximately 0, an eluting solution containing 50 mM Tris-HCl (pH 8.0) and 10 mM reduced glutathione (Wako Pure Chemical Industries) was applied. An eluted fraction was concentrated as follows. The eluted fraction was applied to a Centricon-10 (Millipore) so that each tube contained 2 ml of the eluted fraction, and centrifuged at 10000×g. In order to exchange the buffer, when the volume of the eluted fraction decreased, a solution containing 50 mM Tris-HCl (pH 7.5) and 10 mM CaCl$_2$ was added and the whole centrifuged at 10000×g for approximately 2 hours. This step was repeated until the volume of the eluted fraction reached a lower limit. As a result, 200 μl of an enzyme solution containing approximately 5.8 mg of the fusion protein was obtained from 1 liter of the *E. coli* culture. The density of the protein was measured in accordance with the method described in Lowry, O. H. et al., J. of Biological Chemistry, 193, 265–275 (1951).

(3) Property of the Fusion Protein

A collagenase activity of the enzyme solution prepared in Example 4(2) was measured using a PZ-peptide as described above. A specific activity of the crude extract (i.e., supernatant derived from disrupted transformant cells) prepared in Example 4(1) was 0.002 units/μg protein, and that of the purified enzyme solution was 0.029 units/μg protein. The results showed that the GST-class I collagenase fusion protein was expressed in *E. coli* and the fusion protein was able to be purified effectively and easily without a decrease of the activity.

(4) Recovery of the Purified Enzyme Solution

The enzyme solution prepared in Example 4(2) was again applied to the glutathione sepharose column, and as a result, 94.2% of the fusion protein was obtained after being re-adsorbed, re-eluted with reduced glutathione, and re-collected. The collagenase activity and a pattern of protein bands formed by a 6% SDS-PAGE did not change. Therefore, using the GST-class I collagenase fusion protein, the GST-class I collagenase fusion protein was easily removed from a digestion mixture after a desired protein containing a collagen linker prepared by protein engineering was digested with the collagenase activity of the GST-class I collagenase fusion protein.

Although the present invention has been described with reference to specific embodiments, various changes and modifications obvious to those skilled in the art are deemed to be within the spirit, scope, and concept of the invention.

What we claim is:

1. A class I collagenase of SEQ ID NO: 3.
2. A protein consisting of amino acids 110 to 1118 of SEQ ID NO: 3.
3. A fusion protein of a protein consisting of amino acids 110 to 1118 of SEQ ID NO: 3 and a fusion partner.
4. An isolated DNA encoding a class I collagenase of SEQ ID NO: 3.
5. An isolated DNA consisting of the DNA sequence of SEQ ID NO: 4.
6. An isolated DNA encoding a protein consisting of amino acids 110 to 1118 of SEQ ID NO: 3.
7. An isolated DNA encoding a fusion protein of a protein consisting of amino acids 110 to 1118 of SEQ ID NO: 3 and a fusion partner.
8. A vector comprising the isolated DNA according to claim 4.
9. A vector comprising the isolated DNA according to claim 5.
10. A vector comprising the isolated DNA according to claim 6.
11. A vector comprising the isolated DNA according to claim 7.
12. A transformant comprising the vector according to claim 8.
13. A transformant comprising the vector according to claim 9.
14. A transformant comprising the vector according to claim 10.
15. A transformant comprising the vector according to claim 11.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 37

(B) TYPE: nucleotide
            (C) STRANDEDNESS: single
            (D) TOPOLOGY: linear (xi) SEQUENCE DESCRIPTION: SEQ ID NO:1:

CTAAATCAAC TGCAGGAAGT GGATCCATAG CGAATAC                37

(2) INFORMATION FOR SEQ ID NO:2:

(i) SEQUENCE CHARACTERISTICS:
            (A) LENGTH: 20
            (B) TYPE: nucleotide
            (C) STRANDEDNESS: single
            (D) TOPOLOGY: linear (xi) SEQUENCE DESCRIPTION: SEQ ID NO:2:

CTTGAACTGC AGTTCCTAGC                                    20

(2) INFORMATION FOR SEQ ID NO:3:

(i) SEQUENCE CHARACTERISTICS:
            (A) LENGTH: 1118
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Met Lys Lys Asn Ile Leu Lys Ile Leu Met Asp Ser Tyr Ser Lys Glu
 1               5                  10                  15

Ser Lys Ile Gln Thr Val Arg Arg Val Thr Ser Val Ser Leu Leu Ala
                20                  25                  30

Val Tyr Leu Thr Met Asn Thr Ser Ser Leu Val Leu Ala Lys Pro Ile
            35                  40                  45

Glu Asn Thr Asn Asp Thr Ser Ile Lys Asn Val Glu Lys Leu Arg Asn
        50                  55                  60

Ala Pro Asn Glu Glu Asn Ser Lys Val Glu Asp Ser Lys Asn Asp
 65                 70                  75                  80

Lys Val Glu His Val Lys Asn Ile Glu Glu Ala Lys Val Glu Gln Val
                85                  90                  95

Ala Pro Glu Val Lys Ser Lys Ser Thr Leu Arg Ser Ala Ser Ile Ala
            100                 105                 110

Asn Thr Asn Ser Glu Lys Tyr Asp Phe Glu Tyr Leu Asn Gly Leu Ser
        115                 120                 125

Tyr Thr Glu Leu Thr Asn Leu Ile Lys Asn Ile Lys Trp Asn Gln Ile
    130                 135                 140

Asn Gly Leu Phe Asn Tyr Ser Thr Gly Ser Gln Lys Phe Phe Gly Asp
145                 150                 155                 160

Lys Asn Arg Val Gln Ala Ile Ile Asn Ala Leu Gln Glu Ser Gly Arg
                165                 170                 175

Thr Tyr Thr Ala Asn Asp Met Lys Gly Ile Glu Thr Phe Thr Glu Val
            180                 185                 190

Leu Arg Ala Gly Phe Tyr Leu Gly Tyr Tyr Asn Asp Gly Leu Ser Tyr
        195                 200                 205

Leu Asn Asp Arg Asn Phe Gln Asp Lys Cys Ile Pro Ala Met Ile Ala
    210                 215                 220

Ile Gln Lys Asn Pro Asn Phe Lys Leu Gly Thr Ala Val Gln Asp Glu
225                 230                 235                 240

```
Val Ile Thr Ser Leu Gly Lys Leu Ile Gly Asn Ala Ser Ala Asn Ala
            245                 250                 255

Glu Val Val Asn Asn Cys Val Pro Val Leu Lys Gln Phe Arg Glu Asn
            260                 265                 270

Leu Asn Gln Tyr Ala Pro Asp Tyr Val Lys Gly Thr Ala Val Asn Glu
            275                 280                 285

Leu Ile Lys Gly Ile Glu Phe Asp Phe Ser Gly Ala Ala Tyr Glu Lys
            290                 295                 300

Asp Val Lys Thr Met Pro Trp Tyr Gly Lys Ile Asp Pro Phe Ile Asn
305                 310                 315                 320

Glu Leu Lys Ala Leu Gly Leu Tyr Gly Asn Ile Thr Ser Ala Thr Glu
            325                 330                 335

Trp Ala Ser Asp Val Gly Ile Tyr Tyr Leu Ser Lys Phe Gly Leu Tyr
            340                 345                 350

Ser Thr Asn Arg Asn Asp Ile Val Gln Ser Leu Glu Lys Ala Val Asp
            355                 360                 365

Met Tyr Lys Tyr Gly Lys Ile Ala Phe Val Ala Met Glu Arg Ile Thr
            370                 375                 380

Trp Asp Tyr Asp Gly Ile Gly Ser Asn Gly Lys Lys Val Asp His Asp
385                 390                 395                 400

Lys Phe Leu Asp Asp Ala Glu Lys His Tyr Leu Pro Lys Thr Tyr Thr
                405                 410                 415

Phe Asp Asn Gly Thr Phe Ile Ile Arg Ala Gly Asp Lys Val Ser Glu
            420                 425                 430

Glu Lys Ile Lys Arg Leu Tyr Trp Ala Ser Arg Glu Val Lys Ser Gln
            435                 440                 445

Phe His Arg Val Val Gly Asn Asp Lys Ala Leu Glu Val Gly Asn Ala
    450                 455                 460

Asp Asp Val Leu Thr Met Lys Ile Phe Asn Ser Pro Glu Glu Tyr Lys
465                 470                 475                 480

Phe Asn Thr Asn Ile Asn Gly Val Ser Thr Asp Asn Gly Gly Leu Tyr
            485                 490                 495

Ile Glu Pro Arg Gly Thr Phe Tyr Thr Tyr Glu Arg Thr Pro Gln Gln
            500                 505                 510

Ser Ile Phe Ser Leu Glu Glu Leu Phe Arg His Glu Tyr Thr His Tyr
            515                 520                 525

Leu Gln Ala Arg Tyr Leu Val Asp Gly Leu Trp Gly Gln Gly Pro Phe
            530                 535                 540

Tyr Glu Lys Asn Arg Leu Thr Trp Phe Asp Glu Gly Thr Ala Glu Phe
545                 550                 555                 560

Phe Ala Gly Ser Thr Arg Thr Ser Gly Val Leu Pro Arg Lys Ser Ile
                565                 570                 575

Leu Gly Tyr Leu Ala Lys Asp Lys Val Asp His Arg Tyr Ser Leu Lys
            580                 585                 590

Lys Thr Leu Asn Ser Gly Tyr Asp Asp Ser Asp Trp Met Val Tyr Asn
            595                 600                 605

Tyr Gly Phe Ala Val Ala His Tyr Leu Tyr Glu Lys Asp Met Pro Thr
            610                 615                 620

Phe Ile Lys Met Asn Lys Ala Ile Leu Asn Thr Asp Val Lys Ser Tyr
625                 630                 635                 640

Asp Glu Ile Ile Lys Lys Leu Ser Asp Asp Ala Asn Lys Asn Thr Asp
                645                 650                 655

Tyr Gln Thr His Ile Gln Glu Leu Ala Asp Lys Tyr Gln Gly Ala Gly
```

-continued

```
                 660                 665                 670
Ile Pro Leu Val Ser Asp Asp Tyr Leu Lys Asp His Gly Tyr Lys Lys
                675                 680                 685
Ala Ser Glu Val Tyr Ser Glu Ile Ser Lys Ala Ala Ser Leu Thr Asn
                690                 695                 700
Thr Ser Val Thr Ala Glu Lys Ser Gln Tyr Phe Asn Thr Phe Thr Leu
705                 710                 715                 720
Arg Gly Thr Tyr Thr Gly Glu Thr Ser Lys Gly Glu Phe Lys Asp Trp
                725                 730                 735
Asp Glu Met Ser Lys Lys Leu Asp Gly Thr Leu Glu Ser Leu Ala Lys
                740                 745                 750
Asn Ser Trp Ser Gly Tyr Lys Thr Leu Thr Ala Tyr Phe Thr Asn Tyr
                755                 760                 765
Arg Val Thr Ser Asp Asn Lys Val Gln Tyr Asp Val Val Phe His Gly
                770                 775                 780
Val Leu Thr Asp Asn Ala Asp Ile Ser Asn Asn Lys Ala Pro Ile Ala
785                 790                 795                 800
Lys Val Thr Gly Pro Ser Thr Gly Ala Val Gly Arg Asn Ile Glu Phe
                805                 810                 815
Ser Gly Lys Asp Ser Lys Asp Glu Asp Gly Lys Ile Val Ser Tyr Asp
                820                 825                 830
Trp Asp Phe Val Tyr Gly Ala Thr Ser Arg Gly Lys Asn Ser Val His
                835                 840                 845
Ala Tyr Lys Lys Ala Gly Thr Tyr Asn Val Thr Leu Lys Val Thr Asp
                850                 855                 860
Asp Lys Gly Ala Thr Ala Thr Glu Ser Phe Thr Ile Glu Ile Lys Asn
865                 870                 875                 880
Glu Asp Thr Thr Thr Pro Ile Thr Lys Glu Met Glu Pro Asn Asp Asp
                885                 890                 895
Ile Lys Glu Ala Asn Gly Pro Ile Val Glu Gly Val Thr Val Lys Gly
                900                 905                 910
Asp Leu Asn Gly Ser Asp Asp Ala Asp Thr Phe Tyr Phe Asp Val Lys
                915                 920                 925
Glu Asp Gly Asp Val Thr Ile Glu Leu Pro Tyr Ser Gly Ser Ser Asn
930                 935                 940
Phe Thr Trp Leu Val Tyr Lys Glu Gly Asp Asp Gln Asn His Ile Ala
945                 950                 955                 960
Ser Gly Ile Asp Lys Asn Asn Ser Lys Val Gly Thr Phe Lys Ser Thr
                965                 970                 975
Lys Gly Arg His Tyr Val Phe Ile Tyr Lys His Asp Ser Ala Ser Asn
                980                 985                 990
Ile Ser Tyr Ser Leu Asn Ile Lys Gly Leu Gly Asn Glu Lys Leu Lys
                995                 1000                1005
Glu Lys Glu Asn Asn Asp Ser Ser Asp Lys Ala Thr Val Ile Pro Asn
    1010                1015                1020
Phe Asn Thr Thr Met Gln Gly Ser Leu Leu Gly Asp Asp Ser Arg Asp
1025                1030                1035                1040
Tyr Tyr Ser Phe Glu Val Lys Glu Glu Gly Glu Val Asn Ile Glu Leu
                1045                1050                1055
Asp Lys Lys Asp Glu Phe Gly Val Thr Trp Thr Leu His Pro Glu Ser
            1060                1065                1070
Asn Ile Asn Asp Arg Ile Thr Tyr Gly Gln Val Asp Gly Asn Lys Val
            1075                1080                1085
```

Ser Asn Lys Val Lys Leu Arg Pro Gly Lys Tyr Tyr Leu Leu Val Tyr
    1090                1095                1100

Lys Tyr Ser Gly Ser Gly Asn Tyr Glu Leu Arg Val Asn Lys
1105            1110                1115

(2) INFORMATION FOR SEQ ID NO:4:

(i) SEQUENCE CHARACTERISTICS:
        (A) LENGTH: 3356
        (B) TYPE: nucleotide
        (C) STRANDEDNESS: single
        (D) TOPOLOGY: linear (xi) SEQUENCE DESCRIPTION: SEQ ID NO:4:

| | |
|---|---|
| ATGAAAAAAA ATATTTTAAA GATTCTTATG GATAGTTATT CTAAAGAATC TAAAATTCAA | 60 |
| ACTGTACGTA GGGTTACGAG TGTATCACTT TTAGCGGTAT ATCTTACTAT GAATACTTCA | 120 |
| AGTTTAGTTT TAGCAAAACC AATAGAAAAT ACTAATGATA CTAGTATAAA AAATGTGGAG | 180 |
| AAATTAAGAA ATGCTCCAAA TGAAGAGAAT AGTAAAAAGG TAGAAGATAG TAAAAATGAT | 240 |
| AAGGTAGAAC ATGTGAAAAA TATAGAAGAG GCAAAGGTTG AGCAAGTTGC ACCCGAAGTA | 300 |
| AAATCTAAAT CAACTTTAAG AAGTGCTTCT ATAGCGAATA CTAATTCTGA GAAATATGAT | 360 |
| TTTGAGTATT TAAATGGTTT GAGCTATACT GAACTTACAA ATTTAATTAA AAATATAAAG | 420 |
| TGGAATCAAA TTAATGGTTT ATTTAATTAT AGTACAGGTT CTCAAAAGTT CTTTGGAGAT | 480 |
| AAAAATCGTG TACAAGCTAT AATTAATGCT TTACAAGAAA GTGGAAGAAC TTACACTGCA | 540 |
| AATGATATGA AGGGTATAGA AACTTTCACT GAGGTTTTAA GAGCTGGTTT TTATTTAGGG | 600 |
| TACTATAATG ATGGTTTATC TTATTTAAAT GATAGAAACT TCCAAGATAA ATGTATACCT | 660 |
| GCAATGATTG CAATTCAAAA AAATCCTAAC TTTAAGCTAG GAACTGCAGT TCAAGATGAA | 720 |
| GTTATAACTT CTTTAGGAAA ACTAATAGGA AATGCTTCTG CTAATGCTGA AGTAGTTAAT | 780 |
| AATTGTGTAC CAGTTCTAAA ACAATTTAGA GAAAACTTAA ATCAATATGC TCCTGATTAC | 840 |
| GTTAAAGGAA CAGCTGTAAA TGAATTAATT AAAGGTATTG AATTCGATTT TTCTGGTGCT | 900 |
| GCATATGAAA AAGATGTTAA GACAATGCCT TGGTATGGAA AAATTGATCC ATTTATAAAT | 960 |
| GAACTTAAGG CCTTAGGTCT ATATGGAAAT ATAACAAGTG CAACTGAGTG GCATCTGAT | 1020 |
| GTTGGAATAT ACTATTTAAG TAAATTCGGT CTTTACTCAA CTAACCGAAA TGACATAGTA | 1080 |
| CAGTCACTTG AAAAGGCTGT AGATATGTAT AAGTATGGTA AAATAGCCTT TGTAGCAATG | 1140 |
| GAGAGAATAA CTTGGGATTA TGATGGGATT GGTTCTAATG GTAAAAAGGT GGATCACGAT | 1200 |
| AAGTTCTTAG ATGATGCTGA AAAACATTAT CTGCCAAAGA CATATACTTT TGATAATGGA | 1260 |
| ACCTTTATTA TAAGAGCAGG GGATAAGGTA TCCGAAGAAA AATAAAAAG GCTATATTGG | 1320 |
| GCATCAAGAG AAGTGAAGTC TCAATTCCAT AGAGTAGTTG GCAATGATAA AGCTTTAGAG | 1380 |
| GTGGGAAATG CCGATGATGT TTTAACTATG AAAATATTTA ATAGCCCAGA AGAATATAAA | 1440 |
| TTTAATACCA ATATAAATGG TGTAAGCACT GATAATGGTG GTCTATATAT AGAACCAAGA | 1500 |
| GGGACTTTCT ACACTTATGA GAGAACACCT CAACAAAGTA TATTTAGTCT TGAAGAATTG | 1560 |
| TTTAGACATG AATATACTCA CTATTTACAA GCGAGATATC TTGTAGATGG TTTATGGGGG | 1620 |
| CAAGGTCCAT TTATGAAAA AAATAGATTA ACTTGGTTTG ATGAAGGTAC AGCTGAATTC | 1680 |
| TTTGCAGGAT CTACCCGTAC ATCTGGTGTT TTACCAAGAA AATCAATATT AGGATATTTG | 1740 |
| GCTAAGGATA AAGTAGATCA TAGATACTCA TTAAAGAAGA CTCTTAATTC AGGGTATGAT | 1800 |
| GACAGTGATT GGATGGTCTA TAATTATGGA TTTGCAGTTG CACATTACCT ATATGAAAAA | 1860 |

```
GATATGCCTA CATTTATTAA GATGAATAAA GCTATATTGA ATACAGATGT GAAATCTTAT      1920

GATGAAATAA TAAAAAAATT AAGTGATGAT GCAAATAAAA ATACAGATTA TCAAACCCAT      1980

ATTCAAGAGT TAGCAGATAA ATATCAAGGA GCAGGCATAC CTCTAGTATC AGATGATTAC      2040

TTAAAAGATC ATGGATATAA GAAAGCATCT GAAGTATATT CTGAAATTTC AAAAGCTGCT      2100

TCTCTTACAA ACACTAGTGT AACAGCAGAA AAATCTCAAT ATTTTAACAC ATTCACTTTA      2160

AGAGGAACTT ATACAGGTGA AACTTCTAAA GGTGAATTTA AAGATTGGGA TGAAATGAGT      2220

AAAAAATTAG ATGGAACTTT GGAGTCCCTT GCTAAAAATT CTTGGAGTGG ATACAAAACT      2280

TTAACAGCAT ACTTTACGAA TTATAGAGTT ACAAGCGATA ATAAAGTTCA ATATGATGTA      2340

GTTTTCCATG GGGTTTTAAC AGATAATGCG GATATTAGTA ACAATAAGGC TCCAATAGCA      2400

AAGGTAACTG GACCAAGCAC TGGTGCTGTA GGAAGAAATA TTGAATTTAG TGGAAAAGAT      2460

AGTAAAGATG AAGATGGTAA AATAGTATCA TATGATTGGG ATTTTGTCTA TGGTGCAACT      2520

AGTAGAGGCA AAAATTCAGT ACATGCTTAC AAAAAAGCAG GAACATATAA TGTTACATTA      2580

AAAGTAACTG ACGATAAGGG TGCAACAGCT ACAGAAAGCT TTACTATAGA AATAAAGAAC      2640

GAAGATACAA CAACACCTAT AACTAAAGAA ATGGAACCTA ATGATGATAT AAAAGAGGCT      2700

AATGGTCCAA TAGTTGAAGG TGTTACTGTA AAAGGTGATT TAAATGGTTC TGATGATGCT      2760

GATACCTTCT ATTTTGATGT AAAAGAAGAT GGTGATGTTA CAATTGAACT TCCTTATTCA      2820

GGGTCATCTA ATTTCACATG GTTAGTTTAT AAAGAGGGAG ACGATCAAAA CCATATTGCA      2880

AGTGGTATAG ATAAGAATAA CTCAAAAGTT GGAACATTTA AATCTACAAA AGGAAGACAT      2940

TATGTGTTTA TATATAAACA CGATTCTGCT TCAAATATAT CCTATTCTTT AAACATAAAA      3000

GGATTAGGTA ACGAGAAATT GAAGGAAAAA GAAAATAATG ATTCTTCTGA TAAAGCTACA      3060

GTTATACCAA ATTTCAATAC CACTATGCAA GGTTCACTTT TAGGTGATGA TTCAAGAGAT      3120

TATTATTCTT TTGAGGTTAA GGAAGAAGGC GAAGTTAATA TAGAACTAGA TAAAAAGGAT      3180

GAATTTGGTG TAACATGGAC ACTACATCCA GAGTCAAATA TTAATGACAG AATAACTTAC      3240

GGACAAGTTG ATGGTAATAA GGTATCTAAT AAAGTTAAAT TAAGACCAGG AAAATATTAT      3300

CTACTTGTTT ATAAATACTC AGGATCAGGA AACTATGAGT TAAGGGTAAA TAAATA        3356
```